US010408788B2

United States Patent
Parry-Jones et al.

(10) Patent No.: US 10,408,788 B2
(45) Date of Patent: *Sep. 10, 2019

(54) SPACER FOR SIDE LOADED EWOD DEVICE

(71) Applicant: Sharp Life Science (EU) Limited, Oxford (GB)

(72) Inventors: Lesley Anne Parry-Jones, Oxford (GB); Emma Jayne Walton, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 54 days.

This patent is subject to a terminal disclaimer.

(21) Appl. No.: 15/902,268

(22) Filed: Feb. 22, 2018

(65) Prior Publication Data

US 2019/0017962 A1    Jan. 17, 2019

Related U.S. Application Data

(63) Continuation-in-part of application No. 15/647,547, filed on Jul. 12, 2017, now Pat. No. 10,315,911.

(51) Int. Cl.
    *B81B 1/00*      (2006.01)
    *G01N 27/447*    (2006.01)
    *B01L 3/00*      (2006.01)

(52) U.S. Cl.
    CPC .. *G01N 27/44704* (2013.01); *B01L 3/502715* (2013.01); *B01L 3/502723* (2013.01);
    (Continued)

(58) Field of Classification Search
    None
    See application file for complete search history.

(56) References Cited

U.S. PATENT DOCUMENTS 6,565,727 B1    5/2003  Shenderov
6,911,132 B2    6/2005  Pamula et al.
(Continued)

FOREIGN PATENT DOCUMENTS

EP    2548646    1/2013
GB    2542372    3/2017
(Continued)

OTHER PUBLICATIONS

"Digital microfluidics: is a true lab-on-a-chip possible?", R.B. Fair, Microfluid Nanofluid (2007) 3:245-281).
(Continued)

*Primary Examiner* — Eli S Mekhlin
(74) *Attorney, Agent, or Firm* — Renner, Otto, Boisselle & Sklar, LLP

(57) ABSTRACT

An EWOD device includes a first and second substrate assemblies, and a spacer that spaces apart the first substrate assembly from the second substrate assembly to define a channel between them. The spacer defines fluid input ports that are in fluid communication with the channel, and the spacer is configured for directing fluid from the fluid input ports into the channel. The spacer has a combed spacer configuration to define the fluid input ports, including alternating teeth that extend into the channel from a base region, and the teeth isolate adjacent fluid input ports from each other. The spacer may contact only a portion of the first and second substrate assemblies to form a spacerless region within the EWOD device, and the spacer includes regions that are in contact with both the first and second substrate assemblies and extend into the channel to define a cell-gap of the channel.

22 Claims, 13 Drawing Sheets

(52) U.S. Cl.
CPC .. *B01L 3/502792* (2013.01); *G01N 27/44791* (2013.01); *B01L 2200/027* (2013.01); *B01L 2200/0642* (2013.01); *B01L 2200/0673* (2013.01); *B01L 2200/0684* (2013.01); *B01L 2200/12* (2013.01); *B01L 2300/0816* (2013.01); *B01L 2300/0864* (2013.01); *B01L 2300/161* (2013.01); *B01L 2400/0406* (2013.01); *B01L 2400/0427* (2013.01)

(56) References Cited

U.S. PATENT DOCUMENTS

| | | | |
|---|---|---|---|
| 7,163,612 | B2 | 1/2007 | Sterling et al. |
| 8,686,344 | B2 | 4/2014 | Sudarsan et al. |
| 2007/0075922 | A1 | 4/2007 | Jessop |
| 2012/0111506 | A1 | 5/2012 | Rival |
| 2013/0026040 | A1 | 1/2013 | Cheng et al. |
| 2013/0087458 | A1 | 4/2013 | Mieda et al. |
| 2015/0306598 | A1 | 10/2015 | Khandros et al. |
| 2016/0016170 | A1 | 1/2016 | Lay et al. |

FOREIGN PATENT DOCUMENTS

| | | |
|---|---|---|
| JP | 2005510347 A | 4/2005 |
| JP | 2011252768 A | 12/2011 |
| JP | 2012103252 A | 5/2012 |
| WO | WO 03/045556 A2 | 6/2003 |
| WO | WO 2007046485 | 4/2007 |
| WO | WO 2011020013 | 2/2011 |
| WO | WO 2015164846 A1 | 10/2015 |
| WO | WO 2015/023747 | 2/2016 |
| WO | WO 2016/161400 A1 | 10/2016 |

OTHER PUBLICATIONS

Claims from Parent Case, U.S. Appl. No. 15/647,547.
Extended European Search Report of EP Application No. 18182772.6 dated Sep. 14, 2018.

Fig. 1: PRIOR ART

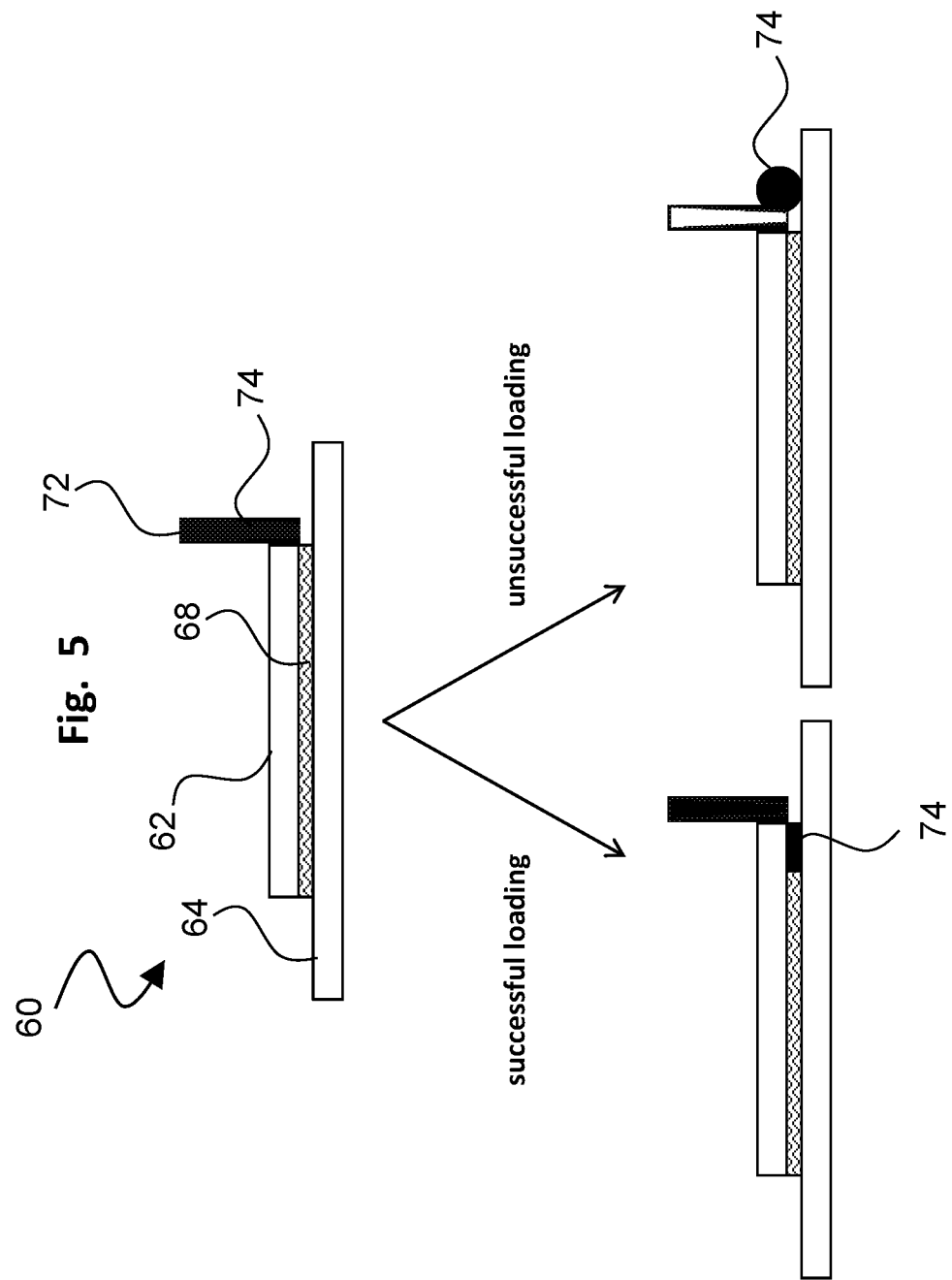

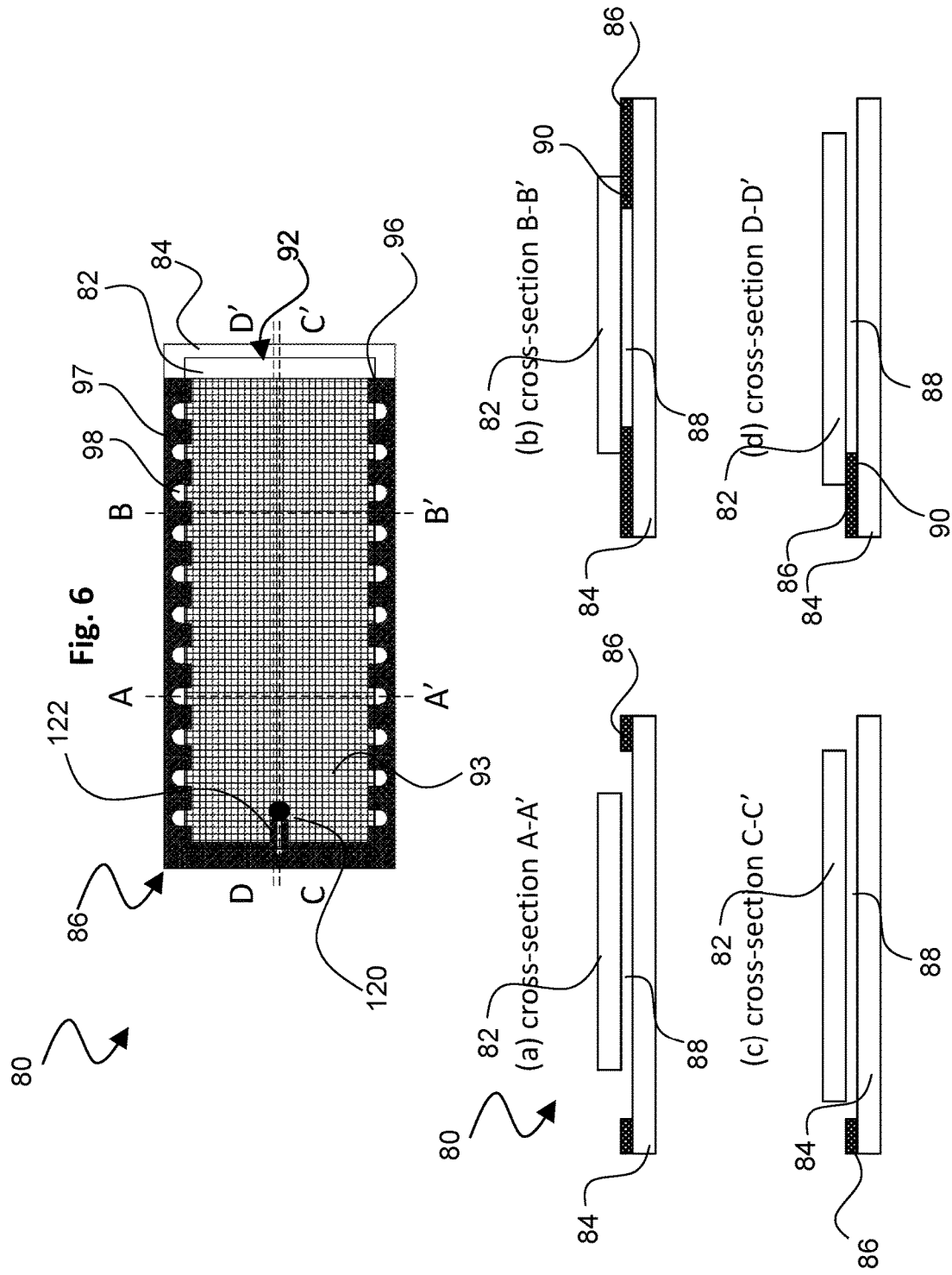

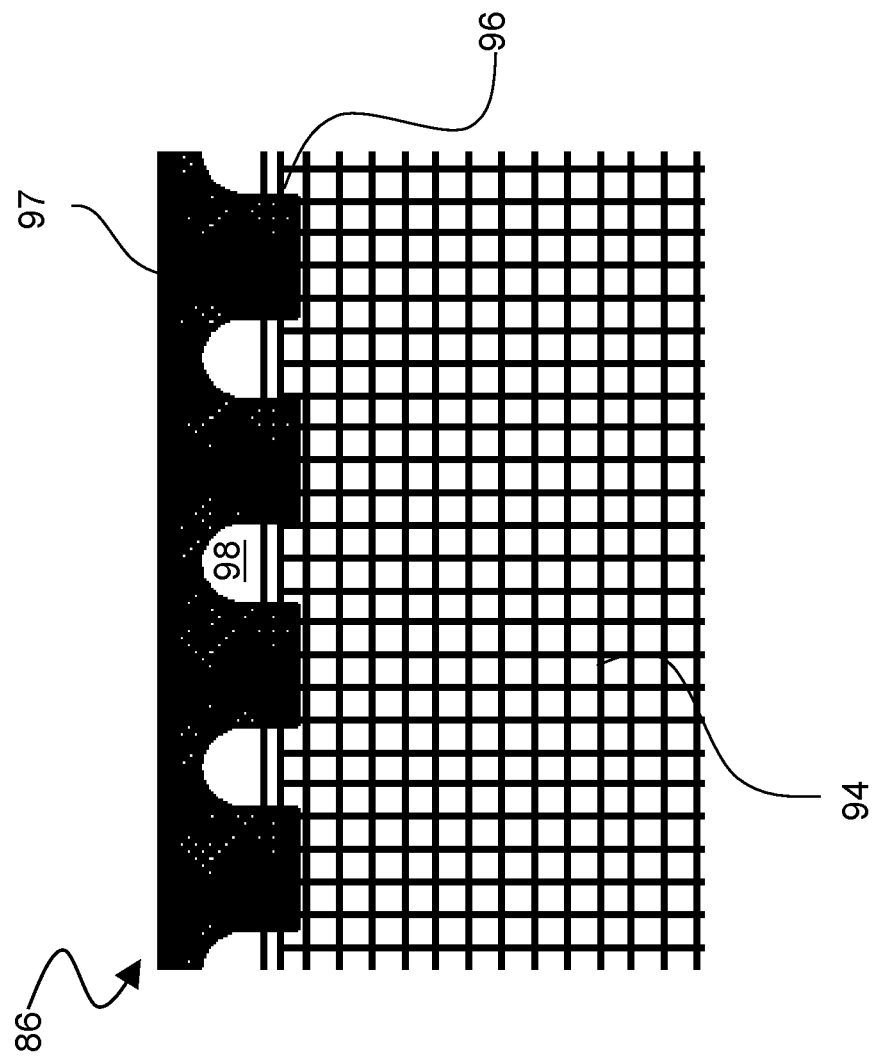

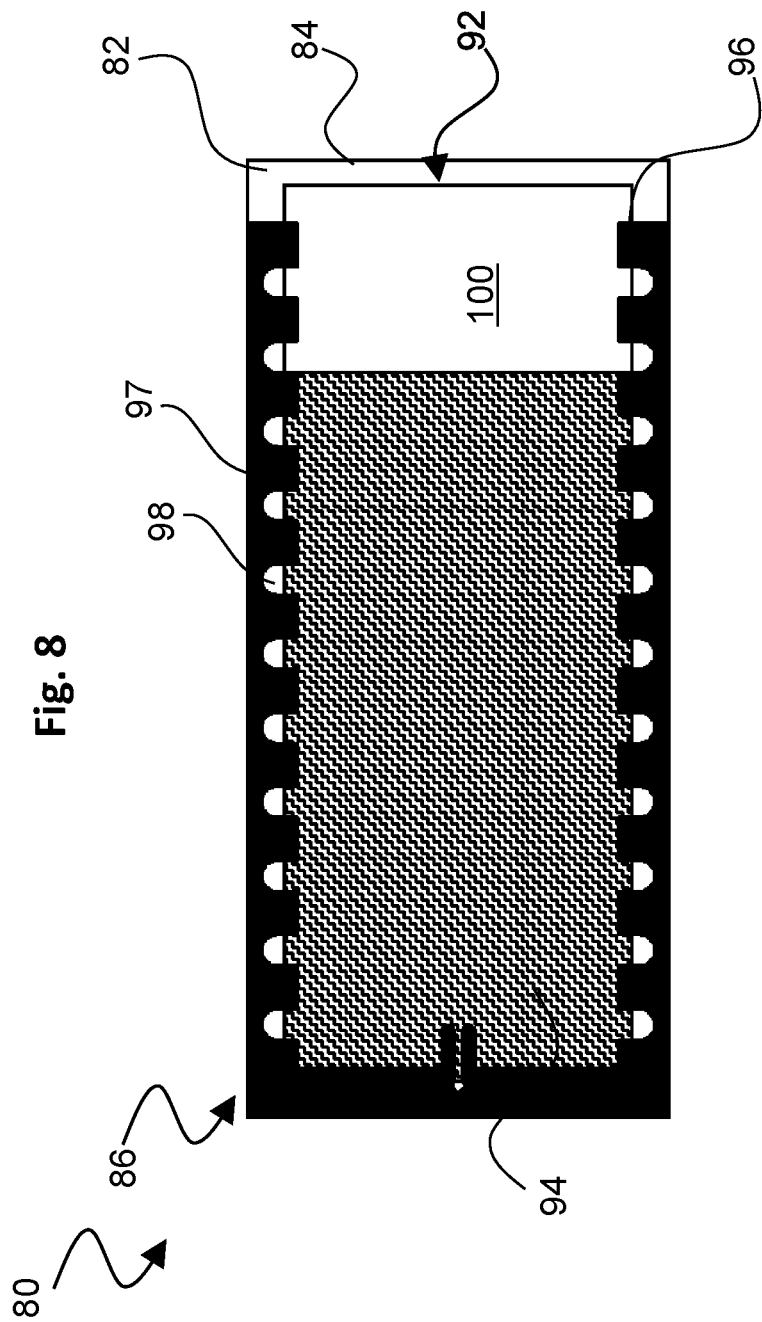

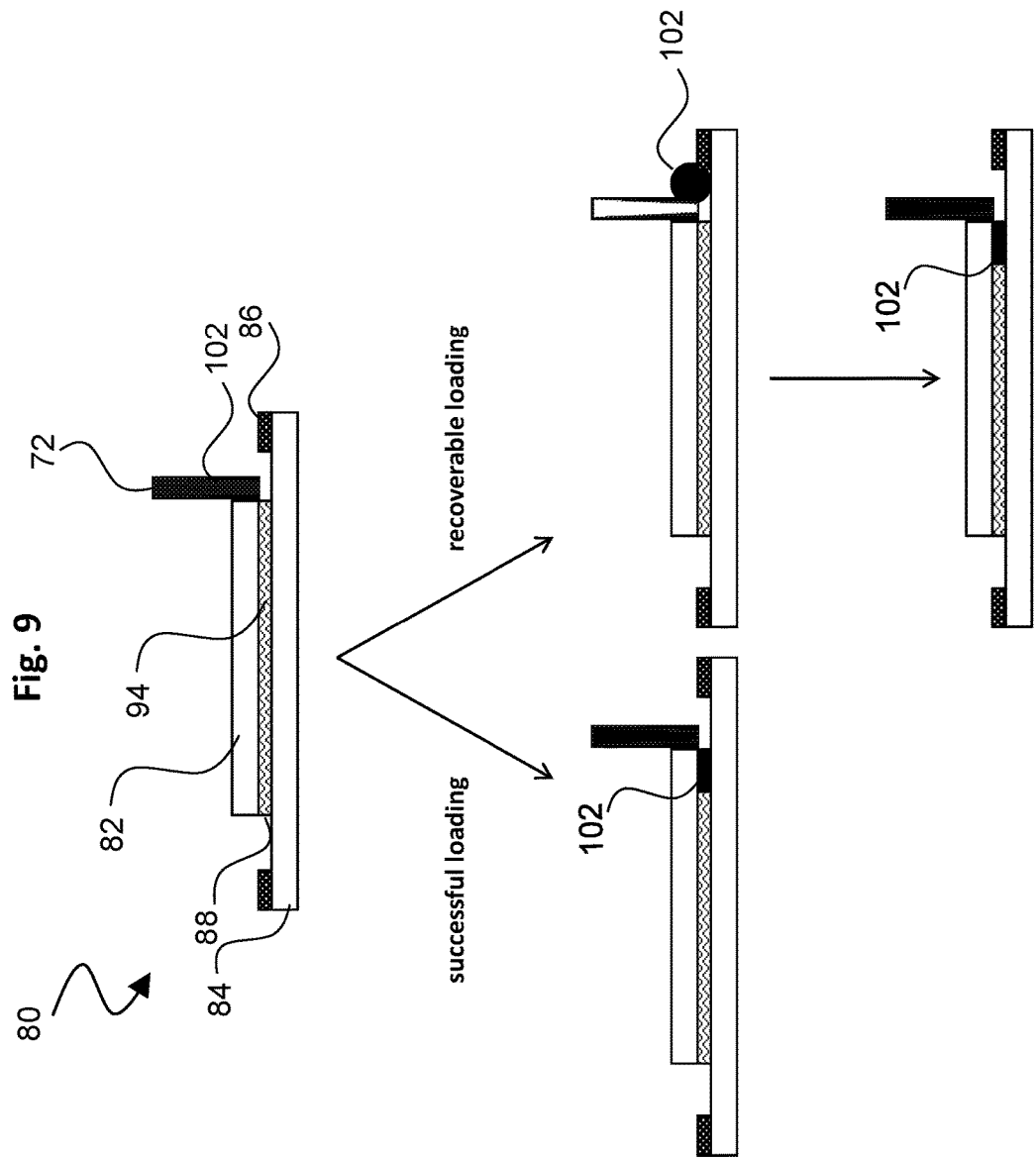

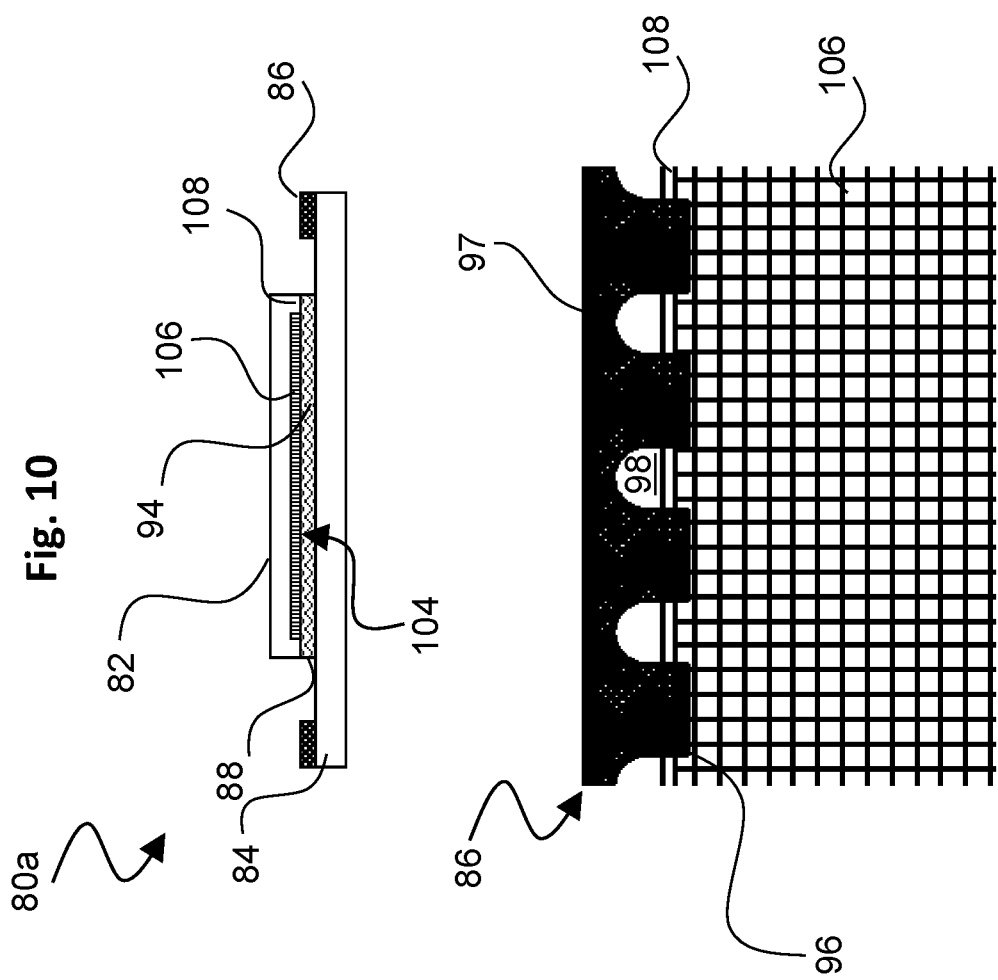

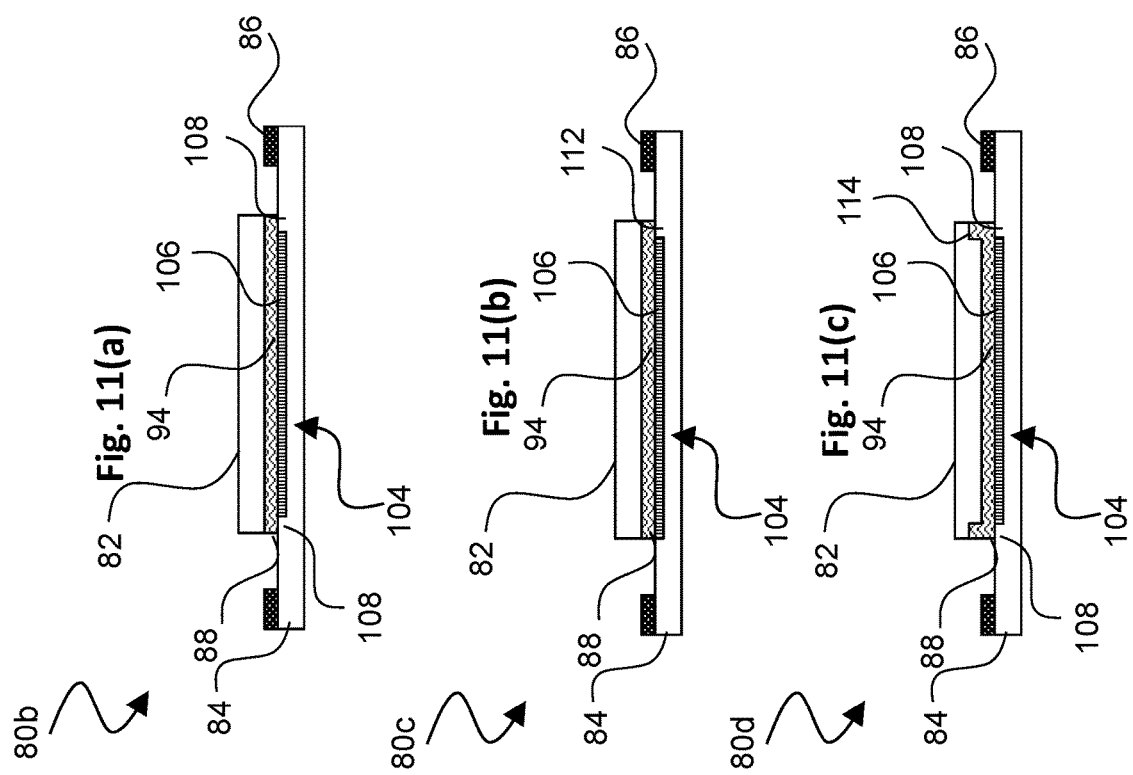

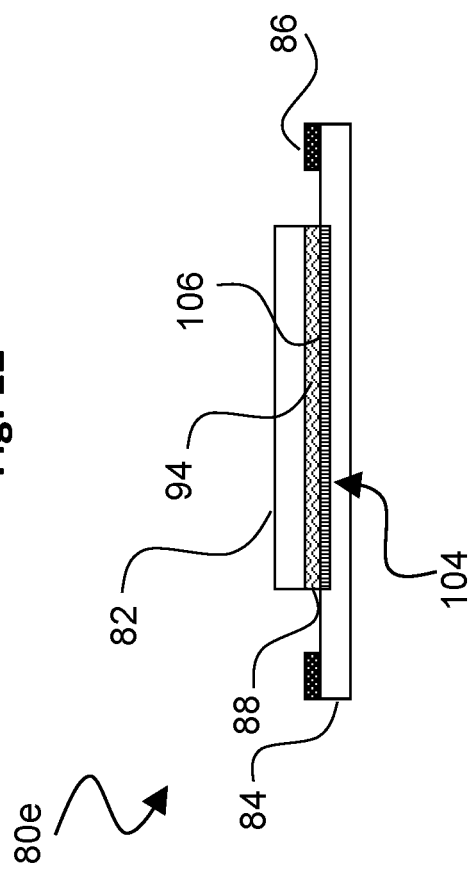

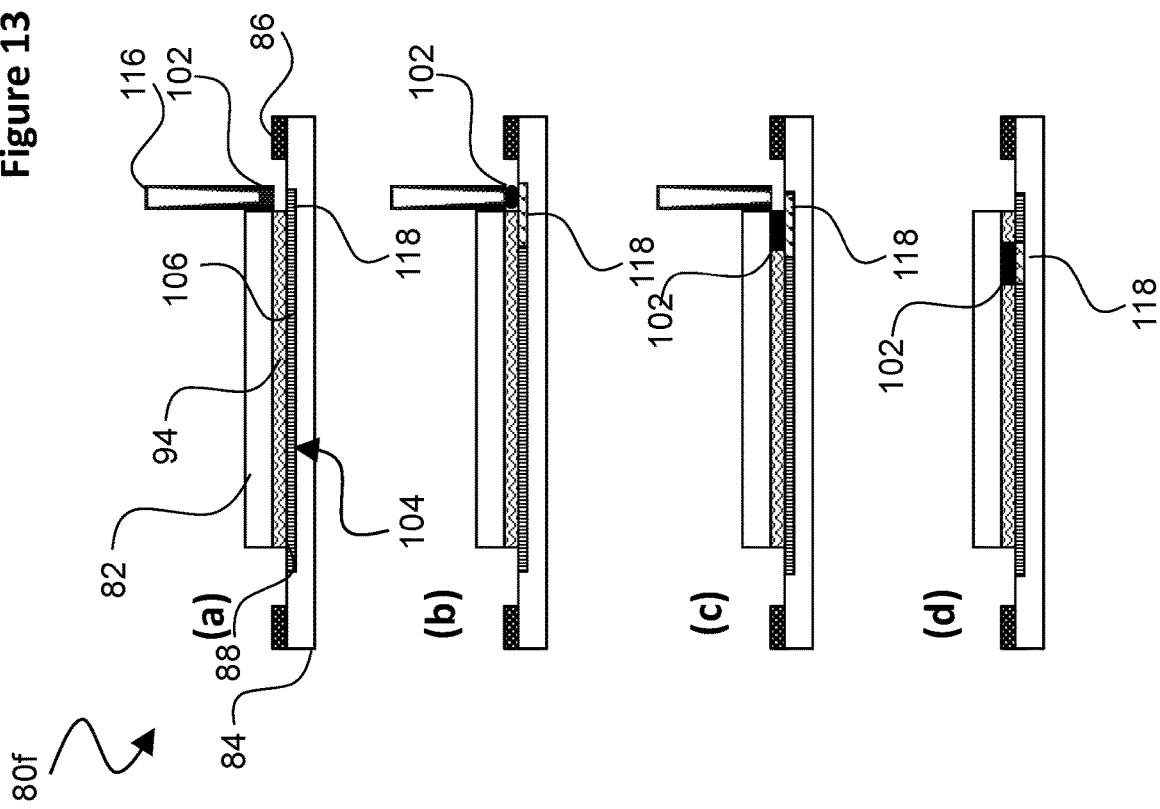

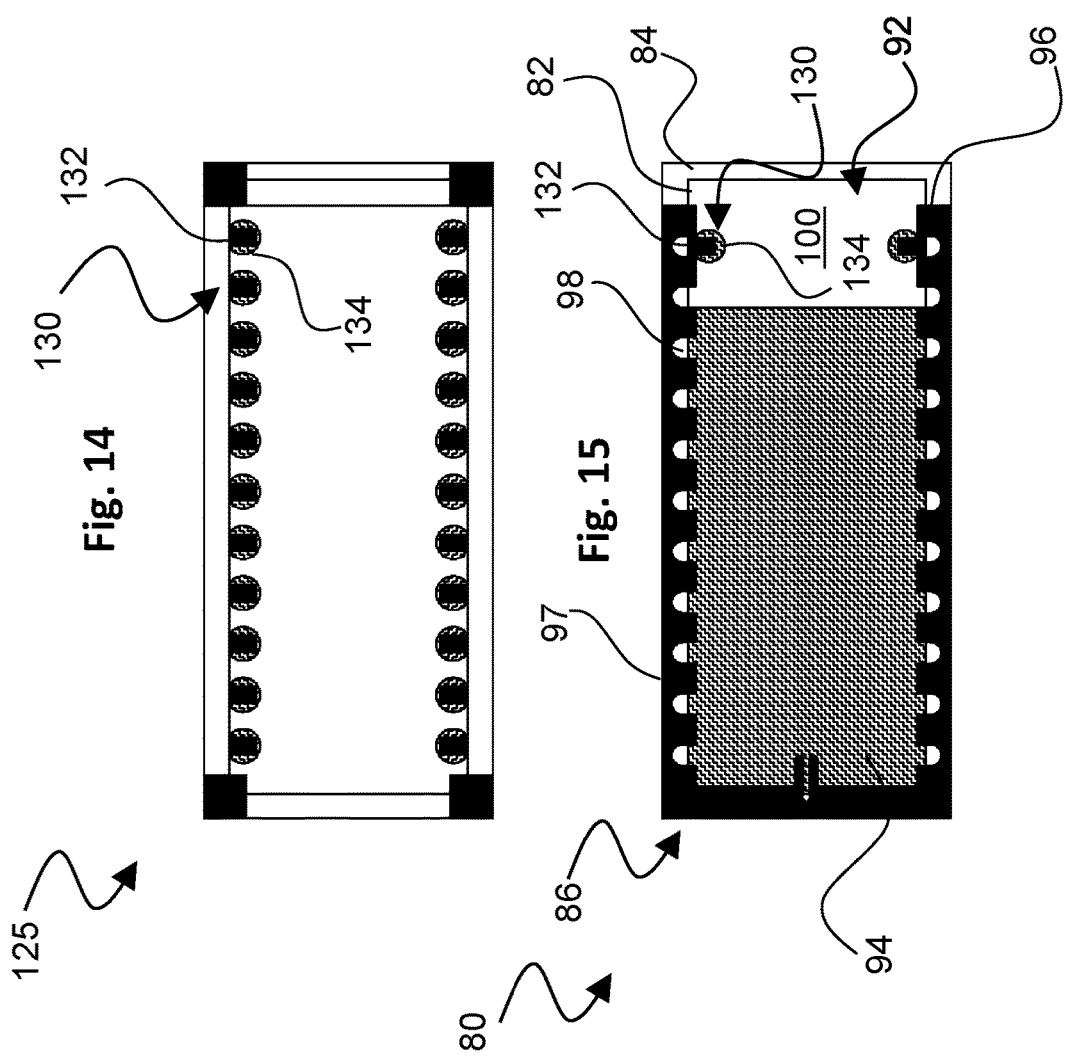

SPACER FOR SIDE LOADED EWOD DEVICE

RELATED APPLICATION DATA

This application is a continuation-in-part application of U.S. application Ser. No. 15/647,547 filed on Jul. 12, 2017, the content of which is incorporated herein by reference.

TECHNICAL FIELD

The present invention relates to droplet microfluidic devices, and more specifically to Active Matrix Electro-wetting-On-Dielectric (AM-EWOD) devices, including input structures for enhanced loading of fluid into such devices.

BACKGROUND ART

Electrowetting on dielectric (EWOD) is a well-known technique for manipulating droplets of fluid by the application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 10, the uppermost layer of which is formed from a conductive material which is patterned so that a plurality of array element electrodes 12 (e.g., 12A and 12B in FIG. 1) are realized. The electrode of a given array element may be termed the element electrode 12. A liquid droplet 14, including a polar material (which is commonly also aqueous and/or ionic), is constrained in a plane between the lower substrate 10 and a top substrate 16. A suitable gap or channel between the two substrates may be realized by means of a spacer 18, and a nonpolar surround fluid 20 (e.g. oil) may be used to occupy the volume not occupied by the liquid droplet 14. The function of the oil is to reduce the surface tension at the surfaces of the polar droplets, and to increase the electro-wetting force, which ultimately leads to the ability to create small droplets and to move them quickly. It is usually beneficial, therefore, for the oil to be present within the channel of the device before any polar fluids are introduced therein.

An insulator layer 22 disposed upon the lower substrate 10 separates the conductive element electrodes 12A, 12B from a first hydrophobic coating 24 upon which the liquid droplet 14 sits with a contact angle 26 represented by θ. The hydrophobic coating is formed from a hydrophobic material (commonly, but not necessarily, a fluoropolymer). On the top substrate 16 is a second hydrophobic coating 28 with which the liquid droplet 14 may come into contact. Interposed between the top substrate 16 and the second hydrophobic coating 28 is a reference electrode 30.

The contact angle θ is defined as shown in FIG. 1, and is determined by the balancing of the surface tension components between the solid-to liquid ($\gamma_{SL}$), the liquid-to non-polar surrounding fluid ($\gamma_{LG}$) and the solid to non-polar surrounding fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \qquad \text{(equation 1)}$$

In operation, voltages termed the EW drive voltages, (e.g. $V_T$, $V_0$ and $V_{00}$ in FIG. 1) may be externally applied to different electrodes (e.g. reference electrode 30, element electrodes 12, 12A and 12B, respectively). The resulting electrical forces that are set up effectively control the hydrophobicity of the hydrophobic coating 24. By arranging for different EW drive voltages (e.g. $V_0$ and $V_{00}$) to be applied to different element electrodes (e.g. 12A and 12B), the liquid droplet 14 may be moved in the lateral plane between the two substrates 10 and 16.

Example configurations and operation of EWOD devices are described in the following. U.S. Pat. No. 6,911,132 (Pamula et al., issued Jun. 28, 2005) discloses a two dimensional EWOD array to control the position and movement of droplets in two dimensions. U.S. Pat. No. 6,565,727 (Shenderov, issued May 20, 2003) further discloses methods for other droplet operations including the splitting and merging of droplets, and the mixing together of droplets of different materials. U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

Electronic driver circuits can be integrated onto the lower substrate 10.
  TFT-based thin film electronics are well suited to the AM-EWOD application. They are cheap to produce so that relatively large substrate areas can be produced at relatively low cost.
  TFTs fabricated in standard processes can be designed to operate at much higher voltages than transistors fabricated in standard CMOS processes. This is significant since many EWOD technologies require electro-wetting voltages in excess of 20V to be applied.

FIG. 2 is a drawing depicting additional details of an exemplary AM-EWOD device 36 in schematic perspective, which may incorporate the layered structures in FIG. 1. The AM-EWOD device 36 has a lower substrate 44 with thin film electronics 46 disposed upon the lower substrate 44, and a reference electrode (comparable to reference electrode 30 above) is incorporated into an upper substrate 54. The electrode configuration may be reversed, with the thin film electronics being incorporated into the upper substrate and the reference electrode being incorporated into the lower substrate. The thin film electronics 46 are arranged to drive array element electrodes 48. A plurality of array element electrodes 48 are arranged in an electrode or element array 50, having X by Y array elements where X and Y may be any integer. A liquid droplet 52 which may include any polar liquid and which typically may be aqueous, is enclosed between the lower substrate 44 and the upper substrate 54 separated by a spacer 56, although it will be appreciated that multiple liquid droplets 52 can be present.

As described above with respect to the representative EWOD structure, the EWOD channel or gap defined by the two substrates initially is filled with the nonpolar fluid (oil). The liquid droplets 14/52 including a polar material, i.e., the droplets to be manipulated by operation of the EWOD device, must be inputted from an external "reservoir" of fluid into the EWOD channel or gap. The external reservoir may for example be a pipette, or may be a structure incorporated into the plastic housing of the device. As the fluid from the reservoir for the droplets is inputted, oil gets displaced and is removed from the EWOD channel.

Different mechanisms have been devised for the inputting or loading of fluid into such devices. For example, U.S. Pat. No. 8,686,344 (Sudarsan et al., issued Apr. 1, 2014) describes a method of fluid loading utilizing patterning of the hydrophobic layers disposed upon the device surfaces. WO 2015/023747 (Yi et al., published Feb. 19, 2016) and US 2016/0016170 (Lay et al., published Jan. 21, 2016) both describe an EWOD cartridge assembly including upper and lower EWOD substrates and a plastic part which functions as a pipette guide.

Achieving entry of the polar fluid into the EWOD channel is non-trivial because the internal surfaces of the EWOD device are hydrophobic. Additionally, the direction of travel of the fluids once in the EWOD channel must be controlled, for example such that different fluids input through different and adjacent ports do not accidentally combine together or mix.

A conventional method of achieving controlled fluid entry is to create an upper substrate with apertures (holes) drilled or otherwise incorporated into the upper substrate. Apertures in the upper substrate provide for convenient fluid input, but of course require the thin film electronics to be on the bottom substrate. The apertures define fluid input ports and a fluid path from the exterior of the EWOD device into the EWOD channel directly above the electrowetting array. Employing apertures in the upper substrate, however, may be difficult and expensive to manufacture, particularly because the preferred material of the upper and lower substrates is glass. Glass is commonly the preferred material because glass is compatible with common LCD manufacturing technologies. It furthermore is advantageous to make the EWOD device with the same materials for the upper and lower substrates to achieve a high precision in the EWOD channel gap, and to minimize deleterious effects of working with different materials of different thermal expansion coefficients for usages in which the device is to be heated. In normal usage, the number of distinct polar fluid entry points is determined by the number of apertures within the upper substrate. As the number of apertures in the upper substrate is increased, both the cost of production and the fragility of the upper substrate goes up.

An alternative approach is to use a side loading configuration that does not require apertures formed in the upper substrate (e.g., the upper substrate is simply rectangular). Fluids that are to enter the EWOD channel are inputted through a side of the EWOD channel between the two substrates, rather than through apertures in the upper substrate. By using an upper substrate with no apertures, the cost and mechanical strength of the upper substrate is completely independent of the number of polar fluid entry points that are required, potentially enabling a higher density of fluid entry points than can be incorporated into the EWOD device when the upper substrate has apertures. It has been difficult, however, to achieve precise control of polar fluid input with current side loading configurations.

GB 2542372 (Walton et al., published Mar. 22, 2017) is another design by the current inventors. Such disclosure describes a method of fluid loading and discloses a spacer design for side-loading of fluid into the EWOD channel. This simple side loading, however, does not incorporate any particular components for ensuring that polar fluid input from outside of the EWOD device is specifically able to enter the EWOD channel.

SUMMARY OF INVENTION

The manner and efficiency of the input of the polar fluid for the liquid droplets can affect the overall performance of the EWOD device. The present invention relates to EWOD and AM-EWOD microfluidic devices, and to controlling the input and output of fluids to and from the hydrophobic EWOD channel defined between the substrate assemblies of such devices. The present disclosure describes an enhanced spacer configuration that permits side loading, and with added structures for ensuring fluid input from outside the EWOD device is able to enter the EWOD channel in a well-controlled manner.

The inventors have recognized that prior side loading designs, while providing advantages over apertures in the upper glass substrate, can encounter deficiencies with respect to how to control the input of the fluids in the case where an incomplete oil filling loading method (as described in GB 2542372) is used. This problem is illustrated, for example, in FIGS. 3 and 4 showing an example of a side loading EWOD device 60 that is insufficient for controlling the position of the air-oil interface when an incomplete oil filling method is to be used. Shown schematically from a top view are an upper glass substrate 62 atop a lower substrate 64, and separated by a spacer 66. An active area of the device 67 (FIG. 3) may be defined as the region containing electrowetting electrodes, atop which liquid droplets may be manipulated. In operation, the droplets are typically manipulated within a non-polar liquid (e.g. oil) as the surrounding medium. It is not necessary, however, that to manipulate droplets the entirety of the active area be filled with oil. Rather, the oil only needs to be present at the boundaries of the liquid droplets. This is exploited in the filling mechanism of the device whereby the channel (optionally including some of the channel that is also the active area) is incompletely filled with oil prior to the polar fluid loading. This incomplete filling by the oil is able to assist in the filling of the polar fluid. Thus, one of the problems being solved by the invention is how to incompletely fill the oil while also ensuring that the oil goes to the correct parts of the channel to assist with the filling of the polar fluid.

In typical operation, the oil is initially loaded into the device. After the initial loading of oil 68, an air bubble 70 will position itself to be along the edges of the upper substrate where the spacer 66 is absent as shown in FIG. 4. If subsequently fluid loading is performed along the edges of the EWOD device where the spacer is absent, proper fluid loading can fail along the edge of the device which has the air bubble.

As an example of successful versus failed side loading, FIG. 5 shows a possible scenario that can occur if the polar fluid is loaded vertically (e.g. via a pipette dock) along the edge that does have the oil present at the air boundary. FIG. 5 depicts a side view of the EWOD device 60 comparable as in FIGS. 3 and 4. A pipette 72 (which may be part of a pipette dock, not shown) may be employed to load the polar fluid 74 into the oil 68. The lower left portion of FIG. 5 shows a successful loading by which the polar fluid 74 comes into contact with the nonpolar fluid (oil) 68, and the polar fluid can be drawn into the EWOD channel using the electrowetting force. However, alternatively a failed loading of the polar fluid 74 can occur in which the polar fluid 74 does not make contact with the oil 68. An unsuccessful fluid loading is shown in the lower right portion of FIG. 5. In such case, the polar fluid may load in the direction away from the upper substrate and EWOD channel and become stranded spaced away from the EWOD channel. If this happens, no contact is made with the oil at the edge of the EWOD channel, and loading of the polar fluid cannot be achieved using the electrowetting force. Previous side loading designs are not configured with appropriate structures to ensure that proper side loading occurs to avoid the unsuccessful loading shown in FIG. 5.

The device of the present disclosure describes structures and related methods of side loading of fluid whereby the above deficiencies associated with prior side loading designs are overcome, and with an EWOD device structure that is simple and compatible with a low-cost assembly process. The described designs include fluid input ports incorporated into a spacer component, configured to facilitate loading of both the polar and nonpolar fluids. The side loading of the present invention has advantageous characteristics. When the EWOD device is initially, and incompletely, filled with the nonpolar filler fluid (oil), the nonpolar filler fluid is presented at positions at which the polar fluid enters via the fluid input ports to ensure contact of the polar fluid with the nonpolar oil. This is significant because contact of the polar fluid with the nonpolar filler fluid provides an enhanced condition for successful loading of the polar fluid into the EWOD channel. When the polar fluid is loaded in a direction that is substantially orthogonal to the EWOD substrates, the polar fluid always enters the EWOD channel without being stranded apart from the EWOD channel as can occur in prior configurations.

The described EWOD device configurations address several significant issues associated with proper loading of fluid into an EWOD device. Such issues include, for example: spacing the EWOD substrates apart uniformly and by the appropriate gap to form the EWOD channel; ensuring that when the device is partially filled with oil that oil will be present at the points at which the polar fluid subsequently is introduced; and controlling the entry of the polar fluid into the EWOD channel of the EWOD device.

An enhanced EWOD device configuration facilitates side loading and resolves the above problems and issues associated with prior designs. In exemplary embodiments, an EWOD device includes a spacer (typically made of plastic). The spacer extends into the EWOD channel between the upper and lower substrates, having at least a spacer part located at least at one edge of the EWOD channel, and the spacer part defines at least one fluid port including an air gap defining an input (or output) from the EWOD channel to the EWOD device exterior.

In other exemplary embodiments, the spacer part may include or perform the functions of one or more of defining the cell gap spacing of the EWOD channel between the upper and lower substrates; defining geometries of fluid input ports optimized for inputting (or outputting) of non-polar (e.g. oil) or polar (e.g. aqueous) fluid input into the EWOD channel; and defining an interface to the outside of the EWOD device for the input and output of fluids from the device, for example pipette guides. The design of the spacer for a given EWOD device may be optimized specific to a design of the active area of the EWOD device; a position of the oil filling port of the EWOD device; points at which polar fluid is subsequently to be loaded in the EWOD channel; a number and volume of separate polar reagents to be loaded into the EWOD channel; and a number and volume of separate polar reagents to be unloaded/extracted from the EWOD channel.

An aspect of the invention, therefore, is an EWOD device that has an enhanced spacer configuration, by which the spacer defines the fluid input ports and is configured in a manner that ensures fluid input from the outside of the device is able to enter the EWOD channel. In exemplary embodiments, the EWOD device includes a first substrate assembly and a second substrate assembly, wherein the first and second substrate assemblies have opposing inner surfaces; and a spacer portion that positions the first substrate assembly and the substrate assembly to space apart the first substrate assembly inner surface from the second substrate assembly inner surface to define a channel between the opposing inner surfaces of the first and second substrate assemblies; wherein the spacer portion defines a plurality of fluid input ports that are in fluid communication with the channel, and the spacer portion is configured for directing fluid from the fluid input ports into the channel. The spacer portion has a combed spacer configuration to define the plurality of fluid input ports, the combed spacer configuration including alternating teeth that extend into the channel from a base region, and the teeth isolate adjacent fluid input ports from each other. The spacer portion may contact only a portion of the first and second substrate assemblies to form a spacerless region within the EWOD device, and the spacer includes regions that are in contact with both the first and second substrate assemblies and extend into the channel to define a cell-gap of the channel.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

BRIEF DESCRIPTION OF DRAWINGS

FIG. 5 is a drawing depicting an exemplary side loading EWOD device illustrating successful and unsuccessful side fluid loading.

FIG. 6 is a drawing depicting a plan view and side cross section views along different sections of a first exemplary EWOD device in accordance with embodiments of the present invention.

FIG. 7 is a drawing depicting a close-up plan view of a portion of the exemplary EWOD device of FIG. 6.

FIG. 8 is a drawing depicting the plan view of the exemplary EWOD device of FIG. 6 with incomplete oil filling.

FIG. 9 is a drawing depicting side views of the exemplary EWOD device of FIG. 6 illustrating successful and recoverable side loading.

FIG. 10 is a drawing depicting a side cross section view and a plan view of another exemplary EWOD device in accordance with embodiments of the present invention.

FIGS. 11(a), 11(b), and 11(c) are drawings depicting side cross-section views of variations of an exemplary EWOD device in accordance with embodiments of the present invention.

FIG. 12 is a drawing depicting a side cross-section view of another exemplary EWOD device in accordance with embodiments of the present invention.

FIGS. 13(a), 13(b), 13(c), and 13(d) are drawings depicting side cross-section views of another an exemplary EWOD device in accordance with embodiments of the present invention, with the figures showing a progression of side fluid loading.

FIG. 14 is a drawing depicting a plan view of an EWOD device using an oil shell method of fluid loading.

FIG. 15 is a drawing depicting a plan view of the exemplary EWOD device of FIG. 6, as shown using an oil shell method of fluid loading.

DESCRIPTION OF EMBODIMENTS

Figure 1:
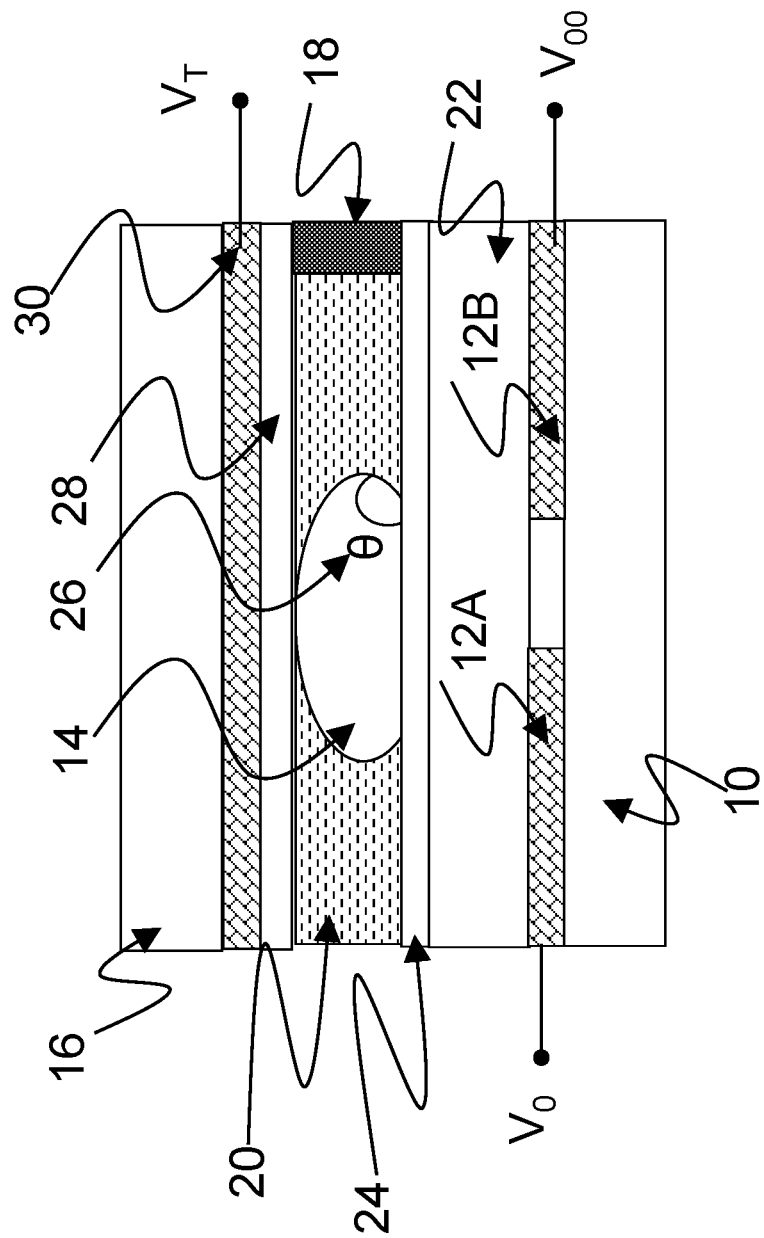
FIG. 1 is a drawing depicting a conventional EWOD device in cross-section.
Figure 2:
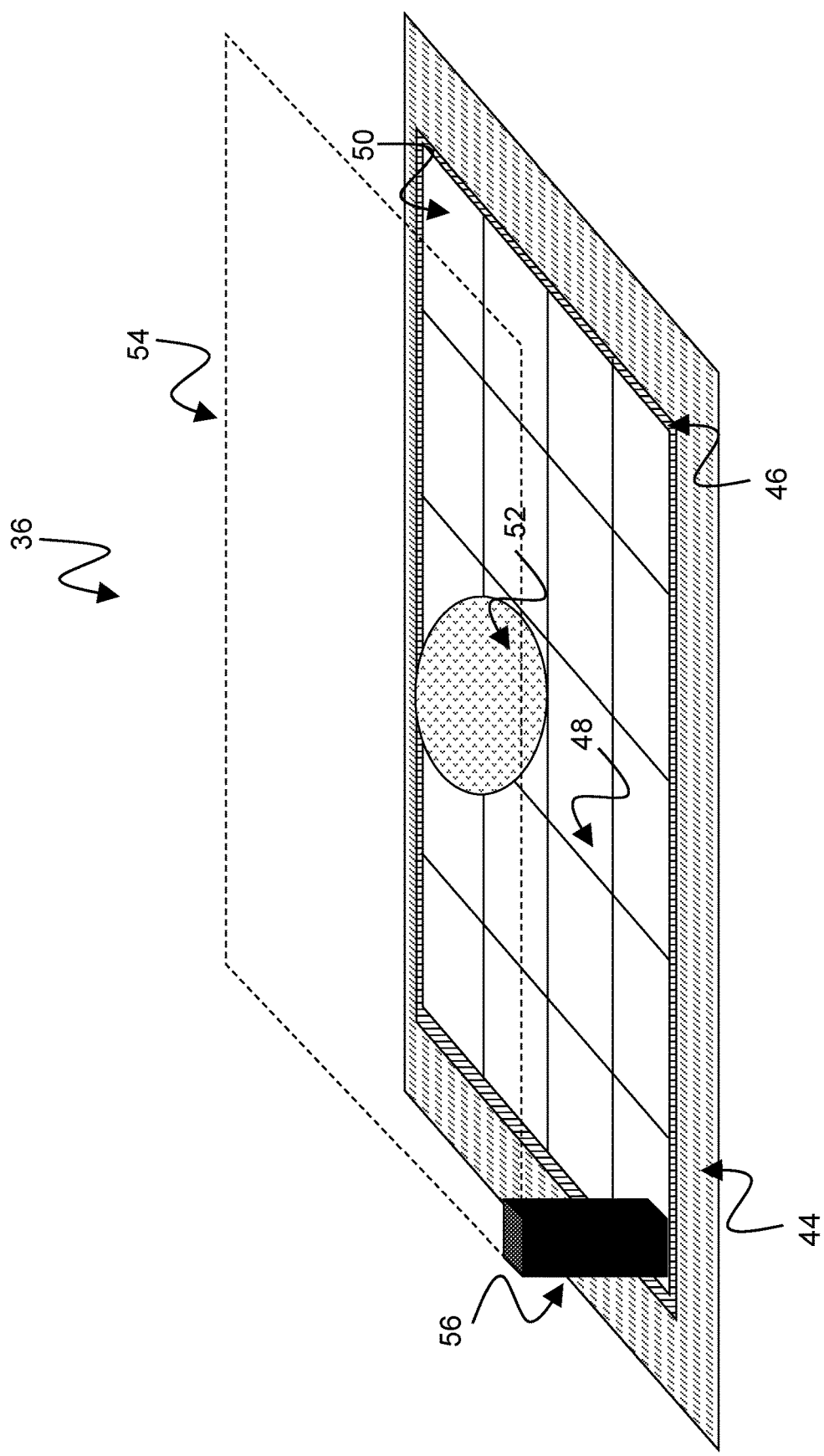
FIG. 2 is a drawing depicting an exemplary AM-EWOD device in schematic perspective.

Embodiments of the present invention will now be described with reference to the drawings, wherein like reference numerals are used to refer to like elements throughout. It will be understood that the figures are not necessarily to scale.

Generally, an aspect of the invention is an EWOD device that has an enhanced spacer configuration, by which the spacer portion defines the fluid input ports and is configured in a manner that ensures fluid input from the outside of the device is able to enter the EWOD channel. In exemplary embodiments, the EWOD includes a first substrate assembly and a second substrate assembly, wherein the first and second substrate assemblies have opposing inner surfaces; and a spacer portion that positions the first substrate assembly and the substrate assembly to space apart the first substrate assembly inner surface from the second substrate assembly inner surface to define a channel between the opposing inner surfaces of the first and second substrate assemblies; wherein the spacer portion defines a plurality of fluid input ports that are in fluid communication with the channel, and the spacer portion is configured for directing fluid from the fluid input ports into the channel. The spacer portion has a combed spacer configuration to define the plurality of fluid input ports, the combed spacer configuration including alternating teeth that extend into the channel from a base region, and the teeth isolate adjacent fluid input ports from each other. The spacer portion may contact only a portion of the first and second substrate assemblies to form a spacerless region within the EWOD device, and the spacer portion includes regions that are in contact with both the first and second substrate assemblies and extend into the channel to define a cell-gap of the channel FIG. 6 is a drawing depicting a top view of an exemplary EWOD device 80 in accordance with embodiments of the present invention. FIG. 6 further shows respectively different cross-sections (a)-(d) of the EWOD device 80 along the lines A-A', B-B', C-C' and D-D'.

The EWOD device 80 includes a first or upper substrate assembly 82 and a second or lower substrate assembly 84. The first/upper and second/lower substrate assemblies have inner opposing surfaces that are separated by a spacer or spacer portion 86 to form a cell gap or EWOD channel 88. In this manner, the spacer/spacer portion 86 positions the first substrate assembly and the substrate assembly to space apart the first substrate assembly inner surface from the second substrate assembly inner surface to define the EWOD channel 88 between the opposing inner surfaces of the first and second substrate assemblies. For simplicity of illustration of pertinent features, the individual layers of the EWOD device components are omitted. Accordingly, the first and second substrate assemblies may include the associated substrate layers, insulating layers, electrode layers, and related structures that form the EWOD device as are known in the art. Typically, the second (lower) substrate assembly 84 constitutes the TFT substrate that would include the thin film electronics, with the first (upper) substrate assembly 82 incorporating the reference electrode. This, however, may be reversed with the first (upper) substrate assembly 82 constituting the TFT substrate and the second (lower) substrate assembly 84 incorporating the reference electrode.

The spacer is configured to have a desired width or thickness so as to correctly position the substrates relative to each other to define an EWOD channel 88 between opposing inner surfaces of the two substrate assemblies. Example materials for the spacer can include suitable rigid sheet plastics, such as for example polycarbonate, PET, polystyrene, polyester, polyimides (e.g. Kapton, Cirlex), or Mylar. The spacer may also have one or more adhesive layers, i.e. be a single or double-sided tape. Alternatively, a spacer portion 86 may be formed integrally with one of the substrate assemblies, and is particularly suitable for fabrication on the lower substrate 84. In integral fabrication embodiments, the spacer portion 86 may be fabricated as an integral part of the lower substrate, such as, for example, being formed from a photoresist or other pattern-able layer that is deposited onto the lower substrate. As such, this layer would be considered part of the lower substrate, and the spacer portion is not provided as a separate component that needs to be assembled and aligned relative to the lower substrate. Rather, for an integral fabrication, alignment of the spacer portion is performed at the point of fabricating said spacer portion (e.g. by photo lithography). Suitable photoresist materials include (but are not limited to) SU8 and Ordyl dry film photoresist. Throughout herein, the terms spacer and spacer portion are used interchangeably as encompassing either a separate element or an integrally fabricated element.

As seen in the cross-section views, the spacer 86 may rest on or be fabricated on one of the substrates, such as the lower substrate 84, and generally may not contact the other substrate, e.g., upper substrate 82, at all surfaces of the spacer. The spacer, however, has at least regions 90 (see cross sections (b) and (d)) that extend into the EWOD channel 88 and thus are in contact with both substrates so as to properly space the substrates apart to form the EWOD channel of a desired width between the inner surfaces of the substrate assemblies. The spacer thereby addresses the issue of spacing the EWOD substrates apart uniformly and with the proper spacing between the opposing inner surfaces to form a suitable cell-gap of the EWOD channel 88.

The spacer 86 is configured for side loading of fluids into the EWOD channel. Accordingly, there is a spacerless region 92 of the EWOD device at which the perimeter of the EWOD device has no spacer portion. The spacerless region 92 is therefore open to air and has no spacer. FIG. 6 shows the device in plan view including an active area 93 as may be filled at least partially with the non-polar fluid or oil. The oil tends to pin to the spacer by capillary action, and thus there is no oil that fills the spacerless region 92. Accordingly, the open spacerless region 92 permits a side loading of polar fluid where the spacer is absent in a well-controlled position and manner.

The spacer 86 is configured as a "combed" spacer including alternating teeth 96 that extend from a base region 97 to define a plurality of fluid input ports 98. FIG. 7 is a drawing depicting a close-up view of a portion of the EWOD device to better illustrate the sub-components of the spacer that form the fluid input ports 98. The teeth 96 extend from the base region 97 into the EWOD channel, and thus provide overlapping regions of the spacer with the oil 94. In the example of FIG. 6, there are twenty-two fluid input ports 98 along the opposing longitudinal sides of the spacer, although any suitable number and location of fluid input ports may be formed. By forming fluid input ports using the combed nature of the spacer 86, the configuration of the EWOD device 80 obviates the need to form fluid input ports by drilling or otherwise providing holes in the either of the glass substrates 82 or 84. Additional details regarding the configuration and functions of the combed spacer and associated fluid input ports are detailed below.

Figure 4:
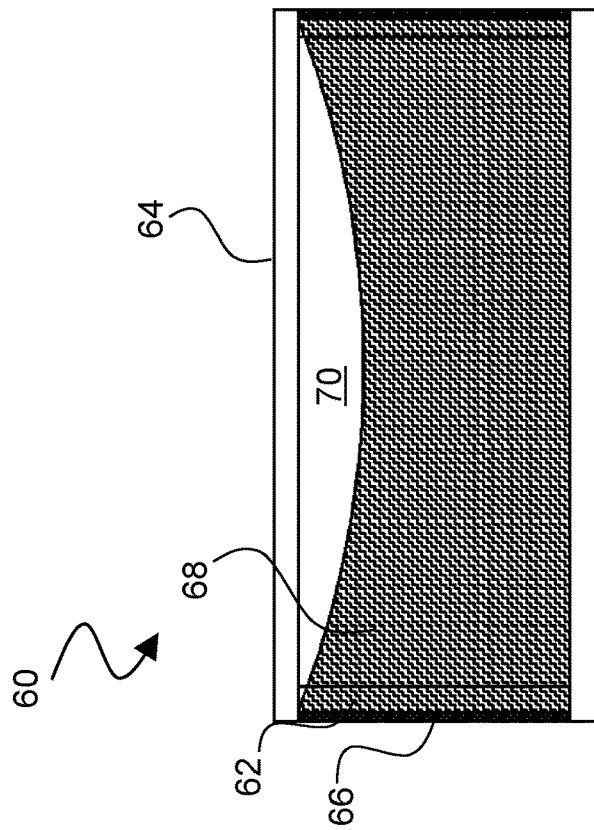
FIG. 4 is a drawing depicting the exemplary side loading EWOD device of FIG. 3 with incomplete oil filling.
Figure 3:
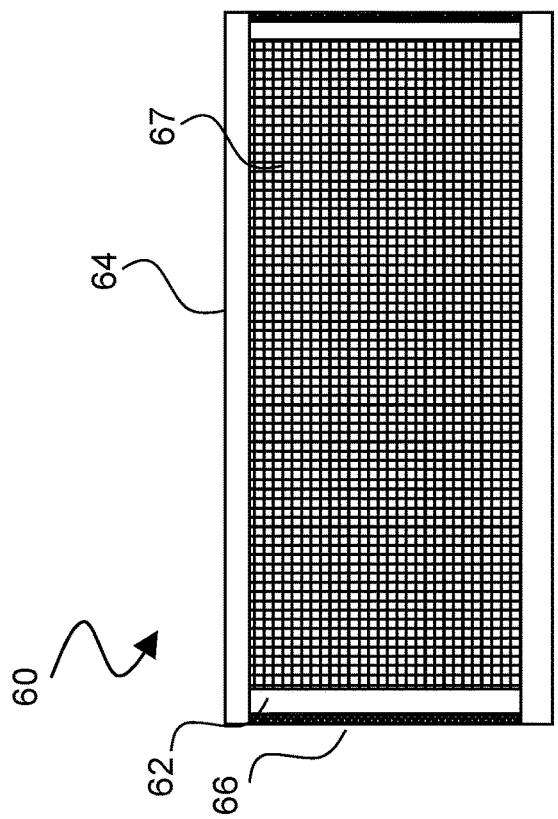
FIG. 3 is a drawing depicting an exemplary side loading EWOD device.

As described above, in certain circumstances it may be desirable to fill the EWOD channel incompletely with oil, which permits the formation of an air bubble comparably as formed in FIG. 4. FIG. 8 is a drawing depicting the EWOD device 80 when the EWOD channel is incompletely filled with oil. When the EWOD channel is incompletely filled with oil, the configuration of EWOD device 80 forms an air bubble 100, the air bubble being formed in a controlled position in the spacerless region 92 to permit in turn well-controlled fluid loading by venting air when oil is displaced by the input of polar fluid.

When incompletely filled with oil, the oil still will tend to pin to those areas of the spacer that overlap with the EWOD channel of the device, and therefore the air bubble 100 will tend to reside at the spacerless region 92 where there is no spacer in the EWOD channel, as shown in FIG. 8. This is useful because it allows polar fluids subsequently to be loaded along the edges of the upper substrate where the combed spacer forms the fluid inputs 98 where polar fluid may be injected. Such configuration performs the function of ensuring that when the EWOD channel is only partially or incompletely filled with oil, oil will be present at points at which the polar fluid subsequently may be inputted into the EWOD channel. When the polar fluid is inputted, oil gets displaced and by virtue of such displacement, air may vent out from the air bubble 100.

As referenced above, the spacer teeth 96 form overlapping regions where the spacer overlaps the oil, and in between the overlapping regions the teeth define the fluid input ports 98. The fluid input ports 98 thus are openings in the spacer that allow polar fluid to enter the device in contact with the oil. Under circumstances in which the polar fluid is loaded at an angle, the polar fluid can easily be injected into the EWOD channel of the device in a well-controlled manner. The combed nature of the spacer also operates such that the polar fluid will not come into contact with parts of the spacer other than the overlapping regions for a controlled fluid input. In other words, the configuration of the teeth 96 and base region 97 confines inputted polar fluid within a particular fluid input port 98 to prevent contact and mixing of different polar fluids.

FIG. 9 is drawing depicting scenarios of fluid input in the EWOD device 80 from a side view, similarly as depicted in FIG. 5, but illustrating how the spacer 86 ensures successful fluid input. The lower left side of FIG. 9 shows ordinary successful fluid loading as would occur when pipetted polar fluid 102 contacts the oil upon input, similarly as the successful loading depicted by the left portion of FIG. 5. Electrowetting forces can be employed to draw the polar fluid into the EWOD channel.

In addition, the configuration of the EWOD device 80 with the spacer 86 further avoids the problem associated with FIG. 5 of the polar fluid potentially being stranded away from the EWOD channel. Rather, the design of the fluid input ports 98 can be tailored to ensure that that any backward flowing fluid will be caught by the spacer and directed into the EWOD channel, referred to herein as "recoverable loading". The lower right portions of FIG. 9 illustrate recoverable loading and how the spacer configuration overcomes the problem associated with unsuccessful loading of prior designs (e.g., FIG. 5). As FIG. 9 shows, provided that sufficient polar fluid 102 is loaded, the teeth and base region of spacer 86 that define the fluid input port will prevent any backward flowing fluid from moving too far from the EWOD channel of the device, as shown in the first step of recoverable loading. Eventually, the fluid issuing from the pipette will touch the oil and enter the EWOD channel of the device before the pipette is retracted as shown in the second step of recoverable loading. What is required is to control the polar fluid so that the polar fluid cannot be loaded into the device without coming into contact with the oil within the EWOD channel. So long as contact with the oil is made, and there exists in the EWOD channel of the device an air bubble (e.g., air bubble 100) that is open to the exterior of the EWOD device so that air can vent from oil displacement by the polar fluid, then the polar fluid will enter the EWOD channel under control of the electrowetting voltage. In this manner, the EWOD device 80 addresses the issue of how to control entry of the polar fluid into the EWOD channel of the device.

The optimum design for the dimensions of the spacer may depend on the dimensions and location of the pipette or other object that is injecting the polar fluid, the angle of fluid injection, the contact angle of the polar fluid with the lower EWOD substrate, and the nature of the polar fluid and its affinity for the spacer material. Typically, there should be one fluid input for 98 in the spacer for each reagent to be injected, and that the smaller the volume to be injected, the closer the back of the spacer should be to the end of the polar fluid injector. In addition, it is typically advantageous to avoid sharp corners in the spacer, for example, by using curved edges or rounded edges where the fluid input ports are defined, as shown for example in the close-up view of FIG. 7. Typically also, independently of the design of the opening part of the spacer, there will be a minimum loadable volume which is determined by the proximity of the polar fluid injector to the edge of the upper EWOD substrate.

A principal advantage of the described configuration is that by defining fluid input ports with the spacer, the requirement for forming holes in the upper or lower substrate is removed. This advantage is particularly appreciable in the case of AM-EWOD devices in which the upper and lower substrates are both preferentially made of glass. This advantage is also particularly appreciable if there is a requirement for the device to have a large number of fluid input ports. Such devices are difficult and expensive to manufacture if the upper substrate has numerous holes, since the holes typically have to be created (e.g. by drilling) one at a time. Numerous holes in the substrate also renders the substrate more fragile This EWOD device 80, enabling side-loading, thus greatly reduces the manufacturing cost of the device while enhancing durability. A further advantage is that the arrangement described facilitates ease of assembly, utilizing the dual function of the spacer to function as both the definer of the EWOD channel gap and the fluid input ports.

The described EWOD device configuration also addresses the significant issues associated with proper loading of fluid into an EWOD device referenced above, including for example: spacing the EWOD substrates apart uniformly and by the appropriate gap to form the EWOD channel; ensuring that when the device is partially filled with oil that oil will be present at the points at which the polar fluid subsequently is introduced; and controlling the entry of the polar fluid into the EWOD channel of the EWOD device. These issues are addressed in a cost-effective manner that is easy to implement without the deficiencies of prior designs.

The spacer 86 also can be configured to enhance fluid extraction to remove processed fluids to permit entry of new polar fluid for droplet manipulations. Referring back to FIG. 6, FIG. 6 illustrates a representative droplet 120 that has been moved to an exit port 122 formed in the spacer 86. In particular, the exit port 122 may be configured as an extension of the spacer that forms a fluid passage into the EWOD channel. Although the exit port 122 is shown as extending from a spacer region that lacks fluid input ports, any suitable location may be employed. In addition, more than one exit port may be provided.

For successful droplet extraction, the port 122 should have an opening that has a diameter or width dimension that is no larger than a diameter of the smallest droplet 120 that may be subject to extraction. When the droplet 120 is moved to the exit port as shown in FIG. 6, the droplet initially blocks the exit port, essentially precluding additional oil from entering the exit port. The polar fluid of the droplet 120 may then be extracted through the exit port by electrowetting or other suitable extraction mechanism. Although a slight amount of the oil that already is within the exit port 122 may be extracted, such amount would be small and negligible, with mainly the polar fluid droplet being subject to extraction.

Such extraction process can also be combined with an adaptive electrode pattern that is applied to the polar droplet being extracted to keep the polar droplet in the correct position within the EWOD channel. Such electrode patterning is described, for example, in Applicant's patent application EP 16194633, which is incorporated here by reference. In this manner, the polar droplet 120 never moves away from the opening in the spacer exit port 122 through which the extraction draw electrowetting force is being applied, which results in a smooth and continuous extraction of the droplet with very little excess oil being drawn out at the same time.

Subsequent figures illustrate structural variations to the above. For ease of illustration, like structures are identified with like reference numerals as in the previous figures and generally are comparably configured. Additional explanation is provided as to the structural differences among the various embodiments. Relatedly, the various embodiments of the EWOD device generally will operate as described above, with certain modifications based on the structural variations as detailed below.

FIG. 10 is a drawing depicting a side view and a plan view (the plan view being a partial and close-up view) of an exemplary EWOD device 80a in accordance with another embodiment of the present invention. In this embodiment, first or upper substrate 82 is the active substrate including thin film drive electronics 104, and the second or lower substrate 84 incorporates the reference electrode. Oil 94 being located with the EWOD channel 88 is shown. This arrangement may be advantageous if the application requires the droplets to be interrogated optically, for example to read out the results of an assay. Depending on the preferred geometry, it may be advantageous to perform optical interrogation of the EWOD device from below, in which case it is advantageous to have the EWOD drive electronics (which are partially absorbing and can be auto-fluorescent) on the upper substrate.

Typically in an AM-EWOD array, it is inconvenient to arrange for the droplet manipulation area of the substrate i.e., the active area, where the surface properties are controllable by electrowetting, to extend right to the edges of the lower substrate. This is due to the need to allow space for row and column driver circuits, and also because there is necessarily some tolerance in the precision to which the glass edge can be defined by the cutting process used to dice individual devices from large mother-glass sources upon which the substrates are typically fabricated.

Accordingly, the EWOD device 80a may include an active area 106 to which electrowetting voltages may be applied, and an inactive border region 108 that is not under active EWOD control. Given this arrangement, the fluid input ports must therefore be sized to receive a minimum volume of polar fluid that must be loaded (for each step of fluid input) to ensure that the fluid input at least partially overlaps the active area 106 of the device. This ensures that the entirety of the fluid input volume can then further be attracted onto the active area 106 by the electrowetting force and then subsequently manipulated in a controlled manner by the EWOD electrodes. To achieve such a configuration, as shown in the plan view, the teeth 96 are configured to extend beyond the inactive region 108 and into the active area 106, which ensures that the fluid input ports 98 are contiguous with the active area. In addition, as referenced above and as shown in FIG. 10 (see also FIG. 7), a portion of a back of the spacer opposite from of the channel that defines the fluid input ports 98 is rounded in shape.

If, for example, a width of the border region is denoted "w" and the cell-gap dimension of the EWOD channel between the two substrates is denoted "d", and with a back portion of the spacer being rounded as shown in FIG. 10, then the fluid input ports must be sized to receive a minimum volume of input fluid that is at least the volume of a disk of radius w/2 and height d, i.e. $\pi dw^2/4$. For example, if the border region is 2 mm wide, and the cell-gap dimension is 250 um, then the minimum polar fluid that can be loaded (and still be useful on the EWOD array) is at least 0.8 ul. Applications which require a volume less than 0.8 ul to be loaded would not be suited to this particular geometry, because the polar fluid may not reach the active area. In applications in which relatively larger volumes of fluid are to be loaded, this geometry has certain advantages, in that the geometry may allow the storage of a certain amount of polar fluid volume within the inactive border region of the EWOD channel of the device, so that if large volumes of polar fluid are required to perform an assay on the EWOD array, the polar fluid can be stored after fluid loading without taking up valuable space on the active area of the device.

For the configuration of FIG. 10, as referenced above it is advantageous to extend the overlap regions of the spacer teeth 96 into the EWOD channel of the device to an extent that the spacer teeth 96 overlap with the active area 106 of the device, again as shown in the plan view of FIG. 10. This further retains different polar fluids isolated from each other in the inactive region 108 of the device in separated fluid input ports 98, so that unwanted mixing of different fluids is prevented.

FIGS. 11(a), 11(b), and 11(c) are drawings depicting side views of different exemplary alternative variations of an EWOD device in accordance with embodiments of the present invention. In these embodiments (in contrast to the previous embodiment), the second or lower substrate 84 is the active substrate including the thin film drive electronics 104, and the first or upper substrate 82 incorporates the reference electrode.

These embodiments demonstrate different variations on how to configure the inactive border region. In the example EWOD device 80b of FIG. 11(a), there is a symmetric inactive border region 108 within the EWOD channel where the upper substrate having the counter electrode extends beyond the edges of the active area 106 of the device, at least on some opposing edges. Because the size of the inactive border region 108 of the EWOD channel is determined by the size and shape chosen for the counter electrode (i.e., not by the design of the drive electronics for the active EWOD array), there is a greater degree of control over the size and shape of the border region. Accordingly, for example in another EWOD device configuration, an asymmetric border region 112 can be configured to have different sizes on differing edges of the device to suit the needs of the fluid volumes to be loaded in a particular application, as shown for example in an exemplary EWOD device 80c shown in FIG. 11(b).

In addition, as referenced above in connection with the previous embodiment, one advantage of having the inactive border region is the potential for storage of larger volumes of polar fluid before the polar fluid is brought onto the active area of the device for droplet operations to be performed. A further advantage of this particular embodiment would be the ease of creating even further volume storage by varying the profile of the upper substrate 82, as shown for example in another exemplary EWOD device 80d shown FIG. 11(c). In such example, the upper substrate 82 has a ridge 114 against which the nonpolar fluid will tend to pin by capillary action to create an additional storage capacity. The ridge 114 is more advantageously formed in the upper substrate 82 because the physical profile of the counter electrode EWOD substrate is more easily varied than the physical profile of the active EWOD substrate.

FIG. 12 is a drawing depicting a side view of another exemplary alternative variation of an EWOD device 80e in accordance with embodiments of the present invention. In this embodiment, again the second or lower substrate 84 is the active substrate including the thin film drive electronics 104, and the first or upper substrate 82 incorporates the reference electrode. The upper substrate 82 is arranged so that along the edges where polar fluid is to be loaded, the edge of the upper substrate is co-incident with the active area 106. In other words, there is no inactive border region along edges of the EWOD device where polar fluid is to be inputted. This arrangement has an advantage in that with no inactive region of the in the EWOD channel where the polar fluid is to be inputted, in principle there is no minimum loadable polar reagent volume as the inputted fluid will always be in contact with the active area. Relatedly, there is no part of the active area of the that is outside the EWOD channel, and so no part of the active area is wasted. As in the previous embodiment, the border region (or lack thereof) can be chosen to be different along different edges of the device, such as in the embodiment of FIG. 11(b), and also may be combined with the variable profile upper substrate to minimize the area taken up by larger volumes of fluid stored on the array, as shown in FIG. 11(c).

FIG. 13 is a drawing depicting a side view of another exemplary alternative variation of an EWOD device 80f in accordance with embodiments of the present invention. In this embodiment, again the second or lower substrate 84 is the active substrate including the thin film drive electronics 104, and the first or upper substrate 82 incorporates the reference electrode. In this example, the upper substrate 82 arranged so that at least part of the active area 106 of the lower EWOD substrate extends beyond the edges of the upper substrate. Such a configuration may be advantageous when very small volumes of fluid are to be loaded into the device, which otherwise may render it more difficult for the inputted fluid to contact the oil or active area. Accordingly, in this embodiment, there always is a portion of the active area EWOD electrodes directly below the fluid injection point, which enables better control of the input of polar fluid at the point where the polar fluid has not yet come into contact with the oil and therefore not yet entered the EWOD channel of the device.

To facilitate the loading of very small volumes of polar fluid, electrode patterns may be synched with the loading of the polar fluid, as shown for example in the progressive series of views (a)-(d) of FIG. 13. In the first view (a), a small volume of polar fluid 102 is located within the injector 116, such as a pipetting device. In the second view (b), initially the small volume of polar fluid 102 exits the injector 116 and does not move laterally due to the small volume. Accordingly, an EWOD electrode portion 118 of the active area 106 is activated in an applied electrode pattern as the polar fluid touches the lower substrate, in readiness to steer the polar fluid 102 towards the EWOD channel before the injector 116 is retracted. As shown in the third view (c), the applied electrode pattern provides an electrowetting force on the polar fluid, which biases a direction of fluid flow towards the EWOD channel of the device (and the oil within), therefore aiding successful loading of small volumes of polar fluid. As shown in the fourth view (d), once the small volume of polar fluid 102 is loaded into the EWOD channel, the injector can be removed from the device. By waiting until the polar fluid has been moved into the EWOD channel before retracting the pipetting device, undesirable backflow of polar fluid upon retraction is avoided, which can occur in conventional configurations.

If the EWOD device includes sensor feedback, this process can be done in an automatic fashion via the use of a software function which automatically detects fluid as soon as it touches the EWOD substrate, and can adapt the applied EWOD electrode pattern in an automated fashion. If the fluid input is being done robotically, this software function can be linked to the pumps so that the injector is only retracted once the polar fluid has safely been moved away from the edge of the EWOD channel. If the fluid input is being done manually (e.g. by pipette) then a signal (audio or visual) can be given to the user when the polar fluid has been moved into the EWOD channel and it is safe to remove the pipette. As in the previous embodiments, the EWOD device 80f can be designed so that this feature is present along only some of the edges of the device, if this suits the fluid loading requirements of the assay to be performed for a given application.

FIGS. 14 and 15 are drawings depicting another exemplary method of employing the EWOD device 80 to input polar fluid into the EWOD channel. In previous embodiments, a feature of the spacer 86 is that the teeth 96 form overlapping regions where the spacer is inside the EWOD channel of the device, and the oil pins oil along the edges of the spacer where fluid inputs are positioned to load the polar fluid. In this manner, the spacer configuration ensures that the polar fluid contacts the oil within the EWOD channel of the device before the object delivering the polar fluid into the EWOD device is retracted.

FIG. 14 depicts an alternative fluid input method referred to herein as an "oil shell" method of fluid input. The oil shell method achieves a comparable effect of contacting the polar fluid and the oil, which negates the need for the oil to be specifically present at the relevant boundary of the upper EWOD substrate and spacer. FIG. 14 depicts a non-specific EWOD device 125 for illustration purposes of the oil shell method. As shown in FIG. 14, in the oil shell method an input droplet 130 is formed including a polar fluid droplet 132 encased within an oil shell 134. If the fluid is to be delivered by pipette, for example, then the input droplet 130 can be formed by dipping the pipette tip into oil after loading the polar fluid into the pipette tip. Alternatively, a double draw can be performed with the pipette, so that two fluids are drawn into the pipette tip including both a controlled quantity of polar fluid simultaneously with a suitable quantity of oil. The two fluids can then be injected into the EWOD channel without the need for oil to be present specifically at the boundary of the input port. The presence of the oil around the polar fluid permits input of the droplet despite the hydrophobicity of the substrate surfaces. Provided the input droplet 130 can be moved by electrowetting forces to the main body of oil or other desired location, proper fluid input is achieved.

FIG. 15 is a drawing depicting the oil shell method as may be employed in connection with the EWOD device 80 shown in FIG. 6. It will be appreciated that the oil shell method comparably may be employed using the EWOD device of any of the described embodiments. As shown in FIG. 15, an oil shell input droplet 130 may be inputted at one of the input ports 98 that is spaced apart from the main body of oil 94. Electrowetting voltages may then be employed to move the input droplet 130 to the main body of oil. The oil shell method may be used in conjunction with the input methods of the other embodiments to load extra polar fluid into any remaining air bubble 100 present in the EWOD device, e.g. such as when insufficient oil 94 has been loaded at the start of a reaction protocol, as shown in FIG. 15.

An aspect of the invention is an EWOD device that has an enhanced spacer configuration, by which the spacer portion defines the fluid input ports and is configured in a manner that ensures fluid input from the outside of the device is able to enter the EWOD channel. In exemplary embodiments, the EWOD device includes a first substrate assembly and a second substrate assembly, wherein the first and second substrate assemblies have opposing inner surfaces; and a spacer portion that positions the first substrate assembly and the substrate assembly to space apart the first substrate assembly inner surface from the second substrate assembly inner surface to define a channel between the opposing inner surfaces of the first and second substrate assemblies; wherein the spacer portion defines a plurality of fluid input ports that are in fluid communication with the channel, and the spacer portion is configured for directing fluid from the fluid input ports into the channel. The EWOD device may include one or more of the following features, either individually or in combination.

In an exemplary embodiment of the EWOD device, the spacer portion has a combed spacer configuration to define the plurality of fluid input ports, the combed spacer configuration including alternating teeth that extend into the channel from a base region.

In an exemplary embodiment of the EWOD device, externally from the channel the teeth isolate adjacent fluid input ports from each other.

In an exemplary embodiment of the EWOD device, the spacer portion contacts only a portion of the first and second substrate assemblies to form a spacerless region within the EWOD device.

In an exemplary embodiment of the EWOD device, the spacer portion includes regions that are in contact with both the first and second substrate assemblies and extend into the channel so as to define a uniform cell-gap of the channel.

In an exemplary embodiment of the EWOD device, the EWOD device further includes an exit port configured as an extension of the spacer portion that forms a fluid passage into the channel.

In an exemplary embodiment of the EWOD device, a portion of the spacer portion opposite of the channel that defines the fluid input ports is rounded in shape.

In an exemplary embodiment of the EWOD device, one of the first substrate assembly or the second substrate assembly includes thin film electronics for applying an electrowetting voltage into the channel, the thin film electronics defining an active area within the channel; and the substrate assembly including the thin film electronics defines an inactive border region adjacent to the active area in which the electrowetting voltage is not applicable.

In an exemplary embodiment of the EWOD device, the spacer portion has a combed spacer configuration to define the plurality of fluid input ports, the combed spacer configuration including alternating teeth that extend into the channel from a base region beyond the inactive border region and into the active area.

In an exemplary embodiment of the EWOD device, if a width of the inactive border region is denoted "w" and a cell-gap dimension of the channel between the first and second substrate assemblies is denoted "d", then the fluid input ports are sized to receive a minimum volume of input fluid of at least a volume of a disk of radius w/2 and height d.

In an exemplary embodiment of the EWOD device, the inactive border region is symmetric on at least some opposing edges of the substrate assembly including the thin film electronics.

In an exemplary embodiment of the EWOD device, the inactive border region is asymmetric to have different sizes on differing edges of the substrate assembly including the thin film electronics.

In an exemplary embodiment of the EWOD device, the substrate assembly including the thin film electronics has a ridge adjacent to the inactive border region.

In an exemplary embodiment of the EWOD device, the first substrate assembly is an upper substrate assembly and includes the thin film electronics.

In an exemplary embodiment of the EWOD device, the second substrate assembly is a lower substrate assembly and includes the thin film electronics.

In an exemplary embodiment of the EWOD device, at least one edge the substrate assembly incorporating the thin film electronics is co-incident with the active area.

In an exemplary embodiment of the EWOD device, one of the first substrate assembly or the second substrate assembly includes thin film electronics for applying an electrowetting voltage into the channel, the thin film electronics defining an active area within the channel; and a portion of the active area extends beyond the substrate assembly including the thin film electronics.

In an exemplary embodiment of the EWOD device, the second substrate assembly is a lower substrate assembly and includes the thin film electronics.

In an exemplary embodiment of the EWOD device, the spacer portion comprises a photoresist layer that is deposited on one of the first substrate assembly or the second substrate assembly.

Another aspect of the invention is a related method of inputting fluid into the EWOD device. In exemplary embodiments, the method of inputting fluid comprising the steps of: inputting a nonpolar fluid into the channel via one of the fluid input ports; inputting a polar fluid into one of the fluid input ports defined by the spacer portion, and the configuration of the spacer portion at the one of the fluid input ports directs the polar fluid to the channel; and applying an electrowetting voltage to move the polar fluid into the channel. The method of input fluid may include one or more of the following features, either individually or in combination.

In an exemplary embodiment of the method of inputting fluid, the spacer portion contacts only a portion of the first and second substrate assemblies to form a spacerless region within the EWOD device, the method further including the steps of: incompletely filling the channel with the nonpolar fluid to form an air bubble within the spacerless region; and inputting a polar fluid into one of the fluid input ports defined by the spacer portion that is at a boundary of where the air bubble and the nonpolar fluid meet.

In an exemplary embodiment of the method of inputting fluid, the spacer portion contacts only a portion of the first and second substrate assemblies to form a spacerless region within the EWOD device, the method further including the steps of: incompletely filling the channel with the nonpolar fluid to form a main body of nonpolar fluid and an air bubble within the spacerless region; forming an input droplet comprising a droplet of the polar fluid encased within a shell of the nonpolar fluid; inputting the input droplet into one of the fluid input ports defined by the spacer that is spaced apart from the main body of the nonpolar fluid; and applying an electrowetting voltage to move the input droplet to come in contact with the main body of the nonpolar fluid.

In an exemplary embodiment of the method of inputting fluid, the method further includes forming the spacer portion from a photoresist layer this is deposited on one of the first substrate assembly or the second substrate assembly.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide an enhanced AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

REFERENCE SIGNS LIST

10—lower substrate
12—array element electrodes
12A—individual array element electrode
12B—individual array element electrode
14—liquid droplet
16—top substrate
18—spacer
20—nonpolar surround fluid
22—insulator layer
24—first hydrophobic coating
26—contact angle
28—second hydrophobic coating
30—reference electrode
36—AM-EWOD device
44—lower substrate
46—thin film electronics
48—array element electrodes
50—electrode or element array
52—liquid droplet
54—upper substrate
56—spacer
62—upper substrate
64—lower substrate
66—spacer
67—active area of the device
68—oil
70—air bubble
72—pipette
74—polar fluid
80/80a-f—EWOD device
82—upper substrate assembly
84—lower substrate assembly
86—spacer/spacer portion
88—EWOD channel
90—regions of spacer
92—spacerless region
93—active area
94—oil
96—spacer teeth
97—spacer base region
98—fluid input ports
100—air bubble
102—pipetted polar fluid
104—thin film drive electronics
106—active area
108—inactive border region
114—ridge
118—EWOD electrode portion
120—droplet
122—exit port
125—EWOD device
130—input droplet
132—polar fluid droplet
134—oil shell

What is claimed is:

1. An electrowetting on dielectric (EWOD) device comprising:

a first substrate assembly and a second substrate assembly, wherein the first and second substrate assemblies have opposing inner surfaces; and a spacer portion that positions the first substrate assembly and the substrate assembly to space apart the first substrate assembly inner surface from the second substrate assembly inner surface to define a channel between the opposing inner surfaces of the first and second substrate assemblies;

wherein the spacer portion defines a plurality of fluid input ports that are in fluid communication with the channel, and the spacer portion is configured for directing fluid from the fluid input ports into the channel; and wherein the spacer portion has a combed spacer configuration to define the plurality of fluid input ports, the combed spacer configuration including alternating teeth that extend into the channel from a base region.

2. The EWOD device of claim 1, wherein externally from the channel the teeth separate adjacent fluid input ports from each other such that adjacent fluid input ports are not in fluid communication with each other except through the channel.

3. The EWOD device of claim 1, wherein the spacer portion contacts only a portion of a perimeter of the first and second substrate assemblies to form a spacerless region in which there is no spacer at the perimeter of the first and second substrate assemblies.

4. The EWOD device of claim 3, wherein the spacer portion includes regions that are in contact with both the first and second substrate assemblies and extend into the channel so as to define a uniform cell-gap of the channel.

5. The EWOD device of claim 1, further comprising an exit port configured as an extension of the spacer portion that forms a fluid passage into the channel.

6. The EWOD device of claim 1, wherein a portion of the spacer portion opposite of the channel that defines the fluid input ports is rounded in shape.

7. The EWOD device of claim 1, wherein:

one of the first substrate assembly or the second substrate assembly includes thin film electronics for applying an electrowetting voltage into the channel, the thin film electronics defining an active area within the channel; and the substrate assembly including the thin film electronics defines an inactive border region adjacent to the active area in which the electrowetting voltage is not applicable.

8. The EWOD device of claim 7, wherein the alternating teeth that extend into the channel form a base region beyond the inactive border region and into the active area.

9. The EWOD device of claim 7, wherein if a width of the inactive border region is denoted "w" and a cell-gap dimension of the channel between the first and second substrate assemblies is denoted "d", then the fluid input ports are sized to receive a minimum volume of input fluid of at least a volume of a disk of radius w/2 and height d.

10. The EWOD device of claim 7, wherein the inactive border region is symmetric on at least some opposing edges of the substrate assembly including the thin film electronics.

11. The EWOD device of claim 7, wherein the inactive border region is asymmetric to have different sizes on differing edges of the substrate assembly including the thin film electronics.

12. The EWOD device of claim 7, wherein the substrate assembly including the thin film electronics has a ridge adjacent to the inactive border region.

13. The EWOD device of claim 7, wherein the first substrate assembly is an upper substrate assembly and includes the thin film electronics.

14. The EWOD device of claim 7, wherein the second substrate assembly is a lower substrate assembly and includes the thin film electronics.

15. The EWOD device of claim 7, wherein at least one edge the substrate assembly incorporating the thin film electronics is co-incident with the active area.

16. The EWOD device of claim 1, wherein:

one of the first substrate assembly or the second substrate assembly includes thin film electronics for applying an electrowetting voltage into the channel, the thin film electronics defining an active area within the channel; and a portion of the active area extends beyond the substrate assembly that does not include the thin film electronics.

17. The EWOD device of claim 16, wherein the second substrate assembly is a lower substrate assembly and includes the thin film electronics.

18. The EWOD device of claim 1, wherein the spacer portion comprises a photoresist layer that is deposited on one of the first substrate assembly or the second substrate assembly.

19. A method of inputting fluid into an electrowetting on dielectric (EWOD) device, the EWOD device comprising:

a first substrate assembly and a second substrate assembly, wherein the first and second substrate assemblies have opposing inner surfaces; and a spacer portion that positions the first substrate assembly and the substrate assembly to space apart the first substrate assembly inner surface from the second substrate assembly inner surface to define a channel between the opposing inner surfaces of the first and second substrate assemblies;

wherein the spacer portion defines a plurality of fluid input ports that are in fluid communication with the channel, and the spacer portion is configured for directing fluid from the fluid input ports into the channel; and wherein the spacer portion has a combed spacer configuration to define the plurality of fluid input ports, the combed spacer configuration including alternating teeth that extend into the channel from a base region the method of inputting fluid comprising the steps of:

inputting a nonpolar fluid into the channel via one of the fluid input ports;

inputting a polar fluid into one of the fluid input ports defined by the spacer portion, and the configuration of the spacer portion at the one of the fluid input ports directs the polar fluid to the channel; and applying an electrowetting voltage to move the polar fluid into the channel.

20. The method of inputting fluid of claim 19, wherein the spacer portion contacts only a portion of the first and second substrate assemblies to form a spacerless region within the EWOD device, the method further comprising the steps of:

incompletely filling the channel with the nonpolar fluid to form an air bubble within the spacerless region; and inputting a polar fluid into one of the fluid input ports defined by the spacer portion that is at a boundary of where the air bubble and the nonpolar fluid meet.

21. The method of inputting fluid of claim 19, wherein the spacer portion contacts only a portion of the first and second substrate assemblies to form a spacerless region within the EWOD device, the method further comprising the steps of:

incompletely filling the channel with the nonpolar fluid to form a main body of nonpolar fluid and an air bubble within the spacerless region;

forming an input droplet comprising a droplet of the polar fluid encased within a shell of the nonpolar fluid;

inputting the input droplet into one of the fluid input ports defined by the spacer portion that is spaced apart from the main body of the nonpolar fluid; and applying an electrowetting voltage to move the input droplet to come in contact with the main body of the nonpolar fluid.

22. The method of inputting fluid of claim 19, further comprising forming the spacer portion from a photoresist layer this is deposited on one of the first substrate assembly or the second substrate assembly.

* * * * *

UNITED STATES PATENT AND TRADEMARK OFFICE
CERTIFICATE OF CORRECTION

PATENT NO. : 10,408,788 B2
APPLICATION NO. : 15/902268
DATED : September 10, 2019
INVENTOR(S) : Lesley Anne Parry-Jones et al.

Page 1 of 1

It is certified that error appears in the above-identified patent and that said Letters Patent is hereby corrected as shown below:

In the Claims

Column 19, Line 5 should read:
"and the second substrate assembly to space apart the first";

Column 20, Line 8 should read:
"edge of the substrate assembly incorporating the thin film";

Column 20, Line 31 should read:
"and the second substrate assembly to space apart the first substrate".

Signed and Sealed this
Ninth Day of June, 2020

Andrei Iancu
*Director of the United States Patent and Trademark Office*